United States Patent
Berthon-Jones et al.

(10) Patent No.: US 6,758,216 B1
(45) Date of Patent: *Jul. 6, 2004

(54) VENTILATORY ASSISTANCE USING AN EXTERNAL EFFORT SENSOR

(75) Inventors: Michael Berthon-Jones, Leonay (AU); Gordon Joseph Malouf, Coogee (AU)

(73) Assignee: ResMed Limited, North Ryde (AU)

( * ) Notice: Subject to any disclaimer, the term of this patent is extended or adjusted under 35 U.S.C. 154(b) by 0 days.

This patent is subject to a terminal disclaimer.

(21) Appl. No.: 09/396,031

(22) Filed: Sep. 15, 1999

(51) Int. Cl.[7] .......................... A61M 16/00; A62B 7/00; F16K 31/02
(52) U.S. Cl. ........................... 128/204.23; 128/204.18; 128/204.21; 600/407; 600/473; 600/534
(58) Field of Search .................. 128/204.18, 204.21, 128/204.23; 600/407, 473, 534

(56) References Cited

U.S. PATENT DOCUMENTS

| | | | |
|---|---|---|---|
| 3,913,563 A | | 10/1975 | Ball |
| 3,993,995 A | | 11/1976 | Kaplan et al. |
| 4,180,059 A | * | 12/1979 | Tiep ............................. 607/42 |
| 4,660,568 A | | 4/1987 | Cosman |
| 4,744,356 A | * | 5/1988 | Greenwood ............ 128/204.23 |
| 5,107,830 A | | 4/1992 | Younes |
| 5,148,802 A | * | 9/1992 | Sanders et al. ......... 128/204.18 |
| 5,195,536 A | | 3/1993 | Silva et al. |
| 5,316,010 A | * | 5/1994 | Brown ........................ 600/632 |
| 5,483,969 A | * | 1/1996 | Testerman et al. ............. 607/42 |
| 5,485,851 A | * | 1/1996 | Erickson ....................... 607/42 |
| 5,513,631 A | * | 5/1996 | McWilliams ........... 128/204.23 |
| 5,522,862 A | * | 6/1996 | Testerman et al. ............. 607/42 |
| 5,540,731 A | * | 7/1996 | Testerman ..................... 607/42 |
| 5,540,733 A | * | 7/1996 | Testerman et al. ............. 607/42 |
| 5,546,952 A | * | 8/1996 | Erickson ....................... 607/42 |
| 5,549,655 A | * | 8/1996 | Erickson ....................... 607/42 |
| 5,632,269 A | * | 5/1997 | Zdrojkowski .......... 128/204.23 |
| 5,791,349 A | | 8/1998 | Shmulewitz |
| 6,029,664 A | * | 2/2000 | Zdrojkowski et al. . 128/204.23 |
| 6,062,216 A | | 5/2000 | Corn |
| 6,095,987 A | | 8/2000 | Shmulewitz et al. |
| 6,292,689 B1 | | 9/2001 | Wallace et al. |
| 6,305,374 B1 | * | 10/2001 | Zdrojkowski et al. . 128/204.21 |
| 6,390,091 B1 | * | 5/2002 | Banner et al. ......... 128/204.21 |
| 6,445,942 B1 | | 9/2002 | Berthon-Jones et al. |

FOREIGN PATENT DOCUMENTS

| | | |
|---|---|---|
| EP | 0 078 677 | 5/1983 |
| WO | PCT/AU97/00517 | 2/1998 |
| WO | WO98/12965 | 4/1998 |

OTHER PUBLICATIONS

Tobin et al., Principles & Practice of Mechanical Ventilation, p. 42, Fig 2–4, 1994.*

* cited by examiner

Primary Examiner—Henry Bennett
Assistant Examiner—Joseph F. Weiss, Jr.
(74) Attorney, Agent, or Firm—Gottlieb, Rackman & Reisman, P.C.

(57) ABSTRACT

An optical sensor mountable on a patient and targets the supranasternal notch for detecting skin movement by dint of reflected light indicating respiratory effort. The sensor is used in conjunction with a ventilator to provide artificial ventilation support.

27 Claims, 6 Drawing Sheets

VENTILATORY ASSISTANCE USING AN EXTERNAL EFFORT SENSOR

FIELD OF THE INVENTION

This invention pertains to the delivery of mechanical ventilation, and more particularly to the delivery of noninvasive ventilatory support for patients with lung disease.

BACKGROUND

A goal of ventilatory support is to reduce the internal work of breathing in subjects with disease of the lungs or chest wall. Typical mechanical ventilators deliver a varying pressure to the airway, for example, via a face mask or nose mask. In a spontaneously breathing patient, a fundamental problem that must be solved is the synchronization of the delivered pressure with the patient's spontaneous efforts. For example, in a typical bilevel ventilator, the mask pressure is switched to a higher pressure, for example, 20 $cmH_2O$, at the moment of detection of patient inspiratory airflow, and a lower pressure, for example, 5 $cmH_2O$, at the moment of cessation of patient inspiratory airflow. There are at least four problems with the use of patient respiratory airflow to trigger the device between the higher and lower pressures:

(1) large and varying leaks cause a discrepancy between patient respiratory airflow (the desired quantity) and mask flow (the measured quantity);

(2) dynamic airway compression and intrinsic positive pressure cause a mis-match between effort (the truly fundamental quantity) and airflow (the measured quantity);

(3) cardiac emptying produces airflow that can be confused with respiratory airflow; and (4) in patients with high airway resistance causing long respiratory system filling and emptying time constants, inspiratory airflow can continue after cessation of inspiratory effort, and expiratory airflow can continue despite recommencement of inspiratory effort.

There are several known ways to find a more direct measure of patient respiratory effort than is afforded by respiratory airflow. One method is to invasively measure intrathoracic pressure, for example, by placing a pressure sensing catheter in the oesophagus. Increasing respiratory effort produces increasing subatmospheric pressure at the sensor. However, this method is too invasive for general use. Another method is to place respiratory movement sensors around the chest wall, typically one around the thorax and one around the abdomen. Suitable sensors use either inductance pneumography, although reasonable signals can be obtained using strain gauges, magnetometers, graphite-in-rubber bands, etc. Unfortunately, none of these methods truly measures respiratory effort as opposed to the resulting chest wall movement, and if the airway is partially or completely occluded, then the signal can greatly diminish in amplitude even though the respiratory effort has actually increased. Also, changes in mechanics with body position or sleep state make these prior art sensors unreliable.

A third method is to use a diaphragm electromyogram as a measure of spontaneous effort, but this is extremely technically demanding, unsuitable for long term use, and difficult to process due to cardiac artifact. A fourth method, taught by McWilliams in U.S. Pat. No. 5,513,631, is to monitor movement of the nostrils, which flare some moments prior to commencement of spontaneous inspiration under some circumstances. Unfortunately, this may not occur in all sleep states, or under conditions of relatively normal respiratory drive, making it less useful as the condition of concern becomes partially treated.

Another fundamental problem is to determine how much support to give, for example, whether to vary the pressure by 15 $cmH_2O$ as in the above example, or a smaller or larger value. Various known methods attempt to tailor the degree of support to suit the patient. One method is to deliver a fixed degree of support using a bilevel ventilator, and to attempt to tailor that degree of support to be best on average for the patient, by aiming to strike a balance between optimizing arterial oxygenation or carbon dioxide level versus providing comfort to the patient. An advantage is that patients are free to take larger or smaller breaths, and at varying rates, which helps with comfort, but a disadvantage is the inability to provide suitable support under varying conditions. Another essentially opposite method is to provide a fixed volume of air per breath (volume cycled ventilator) or a fixed volume per minute (servo ventilator), which is more effective but less comfortable. A pressure support servo ventilator, for example, as taught in PCT Application 97/00631 of Berthon-Jones entitled "Assisted Ventilation to Match Patient Respiratory Need", combines the comfort advantages of a pressure support ventilator with the blood gas optimizing advantages of a servo ventilator (as well as other advantages related to patient-machine synchronization). Still another method, proportional assist ventilation, is described in Younes U.S. Pat. No. 5,107,830. Proportional assist ventilation measures patient respiratory airflow, and provides support for the resistive component of work of breathing proportional to the respiratory airflow, and support for the elastic component proportional to the integral of respiratory airflow. All the above methods still have varying degrees of problems associated with the difficulties of measurement of respiratory airflow under conditions of high leak.

A ventilator, in general, comprises three parts:

(1) a respiratory effort sensor, or a sensor of a surrogate of respiratory effort, (2) a source of breathable gas at a controllable pressure delivered via a mask or similar interface to a patient's airway, and (3) a control that modulates the mask pressure so as to reduce the respiratory effort signal.

Generally, the respiratory effort signal is inferred from a surrogate such as mask pressure or flow. Both are unreliable indicators of effort in the presence of leaks, particularly changing leaks, which are particularly ubiquitous during noninvasive ventilation. They are also unreliable indicators in the presence of intrinsic PEEP (Positive End Expiratory Pressure), which is common in severe lung disease, because effort can precede flow by an appreciable period. They are also unreliable in the presence of a long respiratory time constant, as is universal in obstructive lung disease, because machine-induced pressure changes lead to long-lasting flow changes even when the patient has ceased inspiratory effort. More direct measures of respiratory effort known to be useable for the control of ventilators are either invasive or unreliable or both.

BRIEF DESCRIPTION OF THE INVENTION

The present invention preferably uses a respiratory effort sensor that measures movements of the suprasternal notch in response to respiratory efforts. This effort sensor is disclosed in co-pending application Ser. No. 09/396,032, entitled "Measurement of Respiratory Effort Using a Suprasternal Sensor" and filed on even day herewith.

The first advantage over the use of respiratory airflow or mask pressure as an indicator of respiratory effort is immunity from leak, resulting in better patient-machine synchronization. The second advantage is that the effort signal increases very promptly after onset of muscular inspiratory effort, even in the presence of intrinsic PEEP, again resulting in better patient-machine synchronization. The advantage over the use of measures such as oesophageal pressure or diaphragm electromyogram using oesophageal electrodes is non-invasiveness. The advantage over surface diaphragm or alae nasi electrodes is robustness and ease of use. The advantage over the use of other indirect measures, such as respiratory movement sensors or impedance sensors on the chest, is robustness and ease of use. The chest has at least two degrees of freedom, making such measures unreliable.

The invention also entails use of a novel control mechanism, in which the mask pressure is modulated so as to servo-control the respiratory effort signal to be zero. The respiratory effort signal is any respiratory effort signal that is not derived from respiratory airflow or mask pressure as in the prior art, i.e., any respiratory effort signal that is not a function of measurement on the air breathed by the patient, the preferred sensor being the suprasternal notch sensor mentioned above.

The method of the invention provides all the advantages of proportional assist ventilation, specifically, very precise matching of ventilatory support to respiratory effort under ideal conditions of zero leak and no intrinsic PEEP. In addition, the method is immune to leak, resulting in better patient-machine synchronization. Furthermore, because effort is servo-controlled to be near zero, it is not necessary for the effort signal to be either linear or calibrated, but merely monotonic on effort (a general requirement of any servo control). Similarly, it is possible to achieve near 100% assistance without having to know or estimate the resistance and compliance of the patient's respiratory system, as in those systems that provide proportional assist ventilation.

DETAILED DESCRIPTION OF THE INVENTION

1. Suprasternal Notch Optical Effort Sensor

Figure 1:
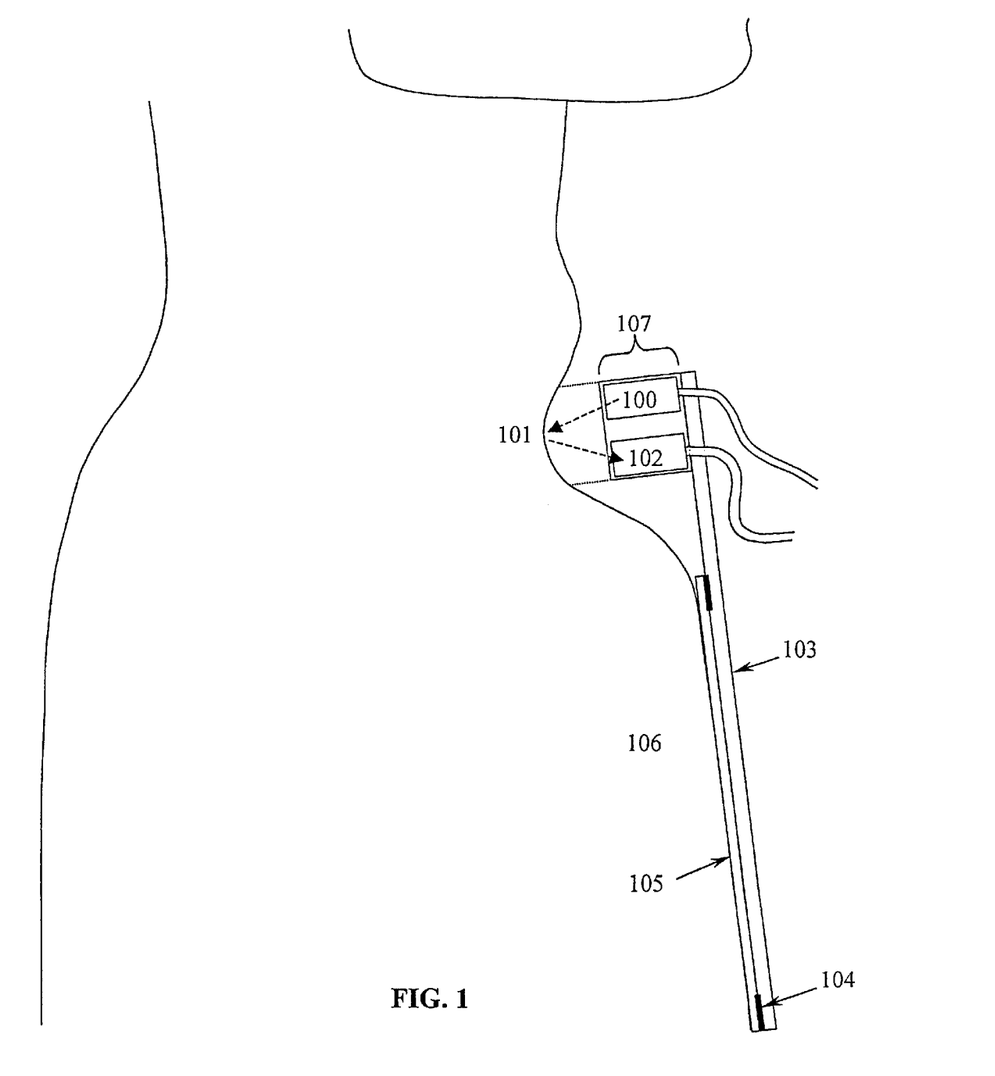
FIG. 1 depicts an optical sensor 107 mounted on the sternum 106, so that the output signal is influenced by the movement of the skin of the suprasternal notch 101.

The preferred embodiment of the present invention uses an optical sensor, such as an infrared proximity sensor, to measure the depth of the suprasternal notch, as shown in FIG. 1. A light source 100 shines light on the skin of the suprasternal notch 101, and the reflected light is received by photocell 102. (The term "photocell" is used to refer to any device whose output is light sensitive, e.g., a photodiode, phototransistor, etc.) The combined sensor assembly 107 may be mounted on any surface which is relatively immobile with respect to the skin of the suprasternal notch, such as the sternum 106. A suitable method for attachment is to mount the sensor 107 on cantilever 103, which is then glued to the sternum using double-sided adhesive tape 104.

Preferably, the double-sided adhesive tape is not glued directly to the skin, but is glued to a layer of soft, spongy, low irritant, low allergenic self-adhesive material 105. A suitable material is DuoDERM®, available from ConvatTec, of Princeton, N.J. The sensor is mounted such that the optical paths of light source and photocell are approximately normal to and centered over the skin at the deepest point of the suprasternal notch. The advantage of the layer of Duo-DERM is that it can remain in place on the skin for long periods, and the sensor can be removed and reapplied multiple times without trauma to the skin. Cantilever 103 can itself be made from a semiflexible material, such as foam or silicone rubber with embedded aluminium reinforcing, so that it can be bent to conform to suit the subject and adjust the distance from the skin of the suprasternal notch. Alternatively, or in addition, sensor 107 can be mounted on the cantilever with adjusting screws so as to adjust the distance of the sensor from the skin of the suprasternal notch. To gain a lower profile, it is convenient to have the optical axis of the sensor parallel with the sternum and use a small mirror to direct the light path at the skin of the suprasternal notch. Another low profile arrangement is to surface mount the sensor electronic components directly onto the cantilever.

Small to moderate inspiratory and expiratory efforts cause quasi-linear movement of the skin of the suprasternal notch, with inspiratory efforts causing the skin to be sucked inwards, away from the sensor, and active expiratory efforts to cause the skin to bulge outwards, towards the sensor. Progressively larger efforts cause progressively smaller increments in skin movement, and efforts of more than about ±10 to 20 $cmH_2O$ pleural pressure produce little further change in the signal. This is convenient, because small efforts produce measurable deformations in the skin, and it is desired to detect small efforts.

Figure 2:
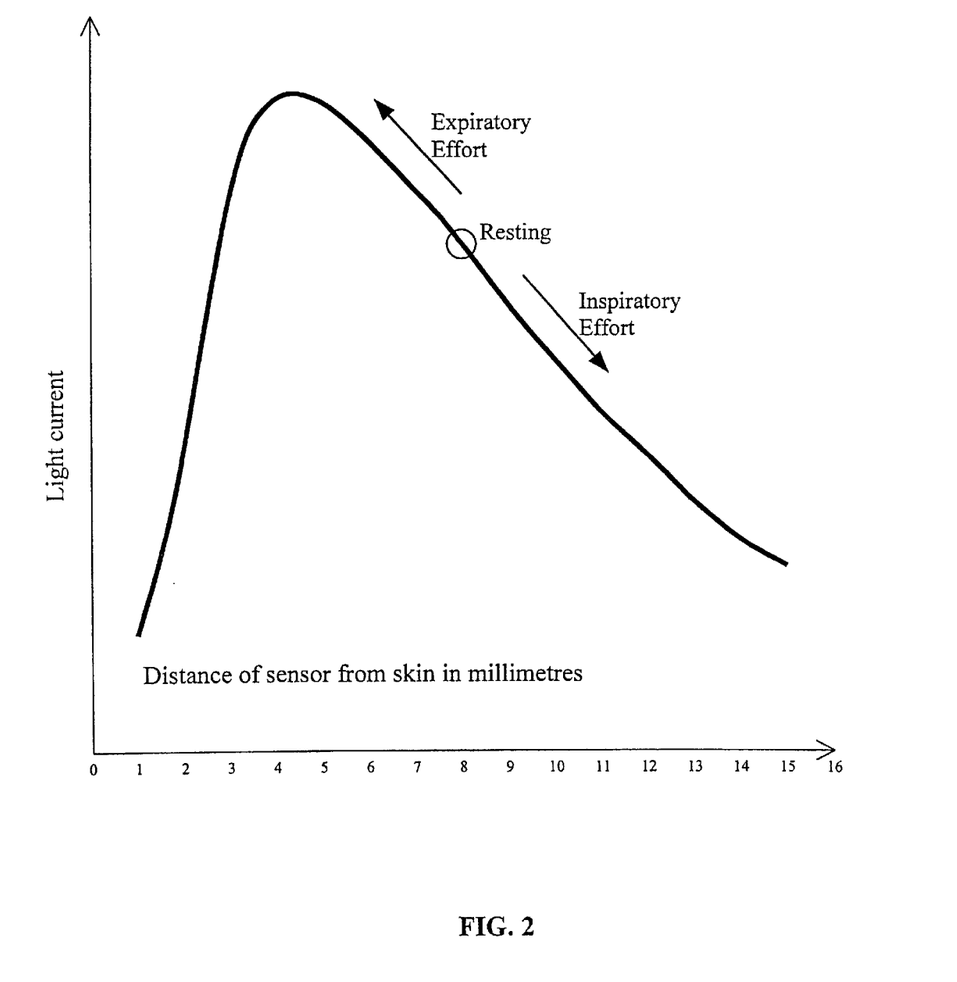
FIG. 2 shows a graph of light current from a commercially available optical sensor as a function of distance between the front of the sensor and the skin. The graph shows how if the sensor is placed at approximately 8 mm from the skin, the signal decreases as the skin is sucked away from the sensor with inspiratory effort, and the signal increases as the skin bulges towards the sensor with expiratory effort.

In a typical arrangement, the light source 100 of the sensor is an infrared light emitting diode, and the photocell 102 of the sensor is a photoresistor, photodiode, or phototransistor. For example, using a commercially available EE-SF5 photomicrosensor available from Omron Corporation, of Kyoto, Japan, the electrical output (light current) increases quasi-linearly for distances from zero to about 4 millimeters, and then decreases quasi-exponentially for distances greater than 5 millimeters, as shown in FIG. 2. (At short distances, a reduced amount of light is detected because of light angle considerations.) Therefore, in the preferred embodiment, the sensor assembly is placed so that the front face of the combined sensor 107 is approximately 8 millimeters from the skin. Inspiratory efforts will cause the distance to increase, resulting in a quasi-exponentially decreasing electrical signal, and expiratory efforts will cause an increasing signal.

In an alternative embodiment, the sensor could be positioned and sized such that it is the ascending portion of the curve of FIG. 2 that is operative, with the light current output increasing with increasing distance.

It is also possible not to glue the cantilever to the skin, but to hold it in place using a bandage, harness, or similar mechanism. Alternatively, the cantilever may be attached to a tight stretch garment such as a Lycra® T-shirt. Combining both alternatives, the cantilever may be mounted on a large disc of soft, thin, high-friction material such as silicone, typically 10 centimeters in diameter, which may be held by friction in contact with the skin by a harness, bandage, stretch Lycra T-shirt, etc. A very low durometer silicone will tend to have a higher coefficient of friction. The large, soft, thin, disc of high friction material may be perforated with multiple holes in order to allow the skin to breathe.

Changes in body posture, for example, turning the head, extending the neck, or rolling from back to side, can change the depth of the suprasternal notch independently of respiratory effort. Therefore, it is desirable to be able to automatically maintain the signal corresponding to zero effort to be zero, independently of (non-breathing related) body changes.

Normally, inspiratory effort is active and expiration is passive. In the preferred embodiment discussed so far using the EE-SF5 sensor, inspiratory effort causes a decreasing light current, as shown in FIG. 2. Therefore, for convenience, the output from the photosensor 102 is inverted, so that inspiration produces a positive signal. This signal is then amplified and zero-adjusted so that zero effort produces an output signal of zero. Changes in posture will tend to change the distance between sensor and skin, which will change the output voltage for zero effort. It is desirable to automatically adjust for such changes in posture, so that zero effort once again produces zero output signal.

Figure 3:
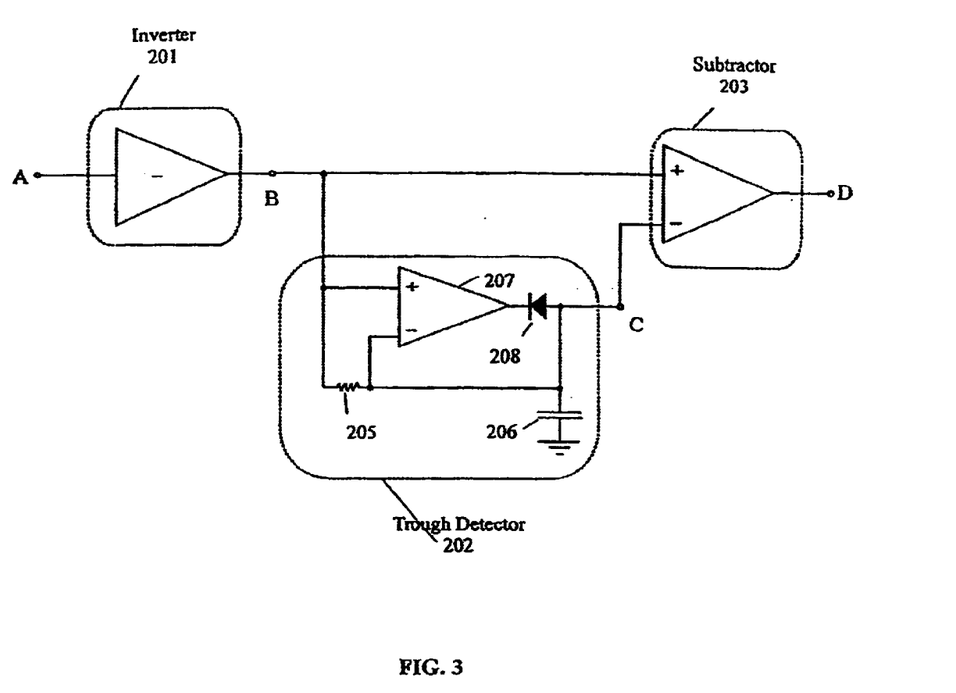
FIG. 3 is a block diagram of processing electronics, including a trough detector to track changes in the light signal even in the presence of body movement, and a subtractor to remove such changes from the signal.

If the optical sensor has been set up so that a positive signal corresponds to inspiratory effort, and if the patient is not making active expiratory efforts, the minimum signal during a breath will correspond to zero effort. A trough detector, comprising a capacitor charged by the sensor output via a resistor, and discharged by the sensor output via a diode, with the resistor-capacitor time constant long compared with a breath but short compared with the interval between postural changes, will track this minimum effort. A suitable time constant is ten seconds. Preferably, the diode is in the feedback loop of an operational amplifier to provide correct operation close to zero signal. A subtractor operational amplifier then subtracts the output of the trough detector from the output from the sensor to yield the effort signal.

Figure 4:
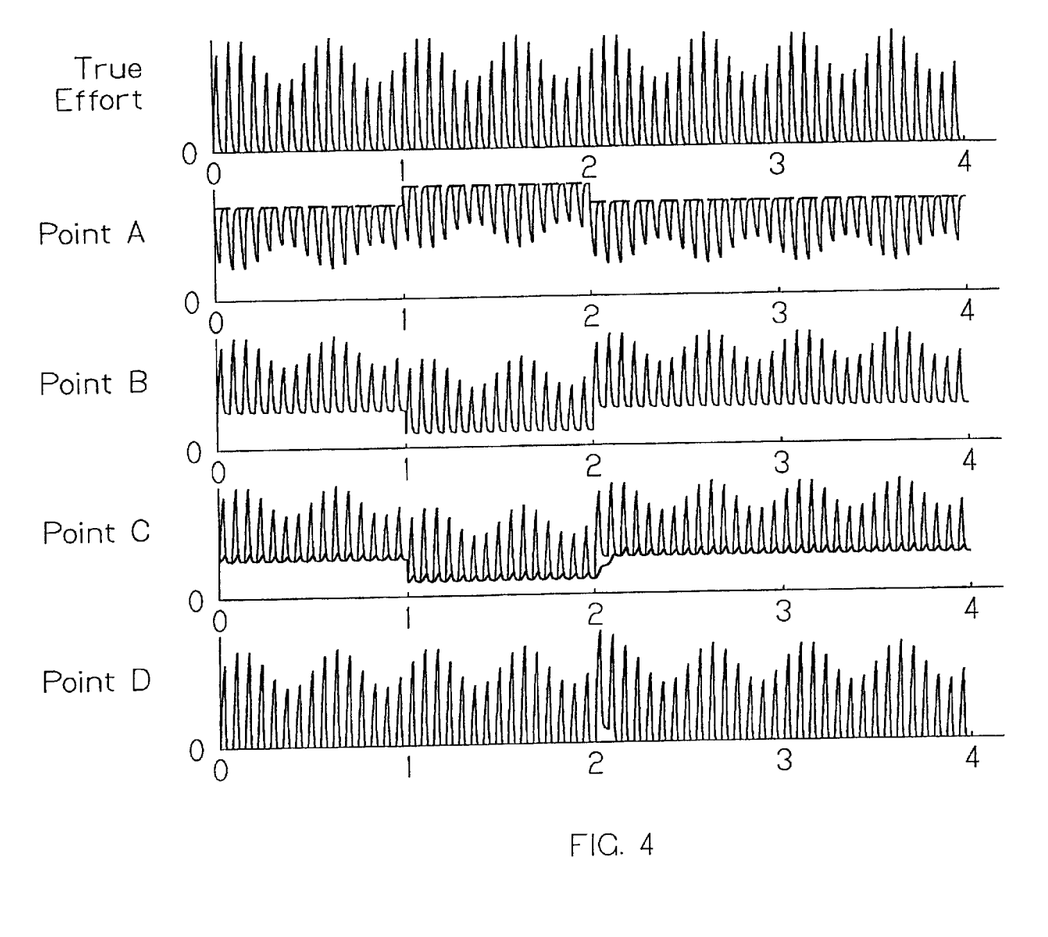
FIG. 4 shows the response of the processing electronics of FIG. 3 to a shift in the signal at minimum effort due, for example, to body movement.

A suitable circuit block diagram for the entire assembly is shown in FIG. 3. Point (A) is the output from a phototransistor or other light-responsive detector, point (B) is the output after inversion by inverter 201, point (C) is the output from the trough detector 202, and point (D) is the zero-corrected effort signal output. FIG. 4 shows the action of the entire assembly. The top tracing is the true respiratory effort, as might be measured using an esophageal pressure transducer, recorded for a period of 4 minutes, or 60 breaths. The peak inspiratory effort varies in amplitude with a period of 30 seconds. The second tracing shows the signal from the phototransistor, at point (A). This signal is upside down, because increasing effort causes the skin to recede from the sensor, causing a reduction in light current from the phototransistor. Thus, zero effort is represented by the flat upper envelope of the waveform at the leading and trailing ends of the tracing.

During the second of the four minutes, the DC offset changes, to simulate the effect of a change in posture leading to the sensor being held closer to the skin (more light output) at zero effort. The third tracing shows the signal at point (B), after inversion. Here, zero effort is represented by the flat lower envelope of the waveform at the leading and trailing ends of the tracing. The heavy line on the fourth tracing shows the signal at point (C), which is the output of the trough detector. For convenience, the signal at point (B) is reproduced as a thin line along with the output of the trough detector. The trough detector tracks the DC shift in the signal during the second minute of the tracing. The reason for this is as follows.

Consider that capacitor 206 has charged through resistor 205 to the potential at point (B). If the potential at point (B) rises above that of the capacitor, the potential at the output of operational amplifier 207 will be greater than that of the capacitor, and diode 207 will be reverse biased. The capacitor potential rises slowly through resistor 205 to the potential at point (B), but it takes several breaths for this to happen. But if the input at point (B) drops below the capacitor level, operational amplifier 207 conducts current through the diode. The capacitor voltage thus decreases rapidly to the lowest level of the input.

The output at point (D) is shown in the bottom tracing—it is the difference (formed in subtractor 203) of the signal at point (B) and the heavy line shown in the tracing for the signal at point (C). The net result is that the final output signal at point (D) is zero for zero effort (along the horizontal axis of the tracing), even if the light output changes due to a change in posture, and the signal increases with increasing effort.

The above functionality can also be performed by a microprocessor which executes a program that samples the sensor output signal, tracks the minimum signal over a moving time window long compared with a breath but short compared with the interval between body movements (such as 10 seconds), and subtracts the minimum signal from the sensor output signal to yield the effort signal.

2. Triggering Using the Suprasternal Notch Sensor

Figure 5:
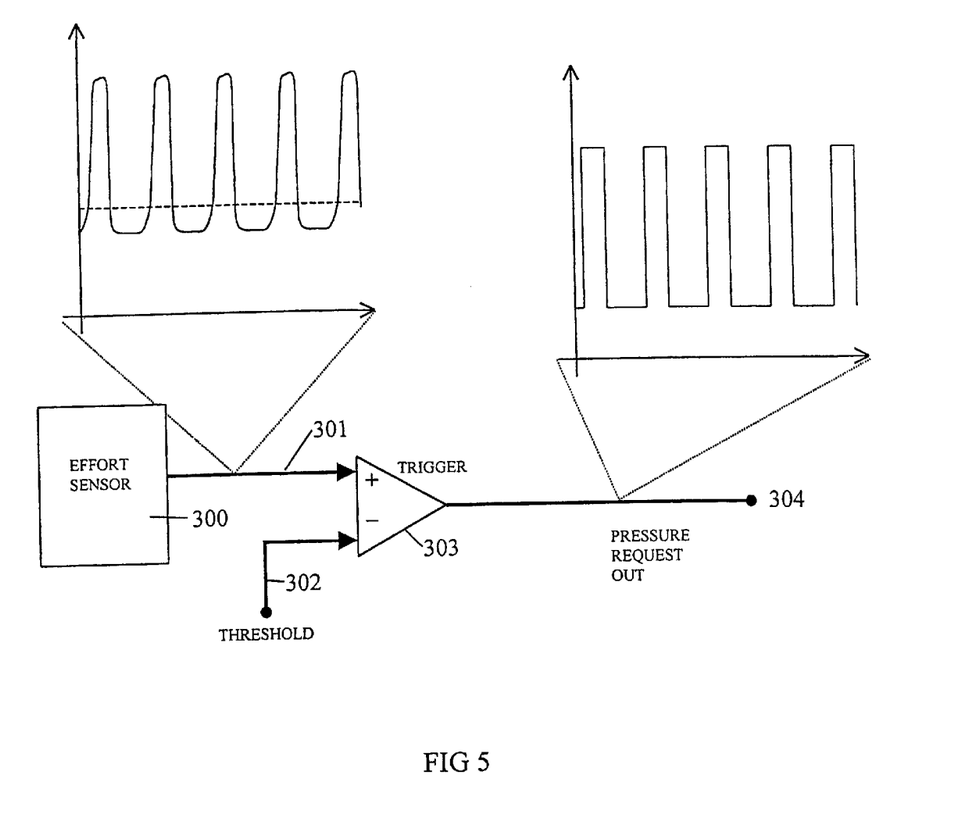
FIGS. 5 and 6 comprise the illustrative embodiments of the invention, in which the block diagram circuit of FIG. 5 uses the preferred respiratory effort sensor of FIGS. 1–4 (shown generally by the numeral 300) to produce a signal 301 that is an increasing function of effort and that is compared with a threshold level 302 (indicated by the dotted line on signal 301) by trigger circuit 303 to produce a pressure request output signal 304, and the pressure delivery system of FIG. 6 includes a pressure request input 400 (from FIG. 4) to servo 401 whose output 402 controls pressure source 403 that delivers breathable gas via hose 404 to mask 405 nd exhaust vent 406, with pressure sensor 408 measuring mask pressure via hose 407, and the output 409 from the pressure sensor providing feedback to the servo 401.

The signal from the optical sensor may be used to trigger a conventional ventilator instead of the ventilator's usual triggering means. In one embodiment, the effort sensor is combined with a prior art spontaneous mode bilevel ventilation control—the mask pressure is set to a high pressure (such as 20 cmH$_2$O) if the effort signal exceeds a threshold, and set to a low pressure (such as 4 cmH$_2$O) otherwise. A block diagram of such an arrangement is shown in FIG. 5. Effort sensor 300 (the device of FIGS. 1–4) supplies zero and body position corrected effort signal 301 to trigger circuit 303, which produces pressure request output signal 304. As shown by the two functions depicted in the drawing, if the input exceeds the threshold on conductor 302, the pressure request signal is set to a high value, and to a low value otherwise. These two values control the two pressures of a conventional ventilator.

Figure 6:
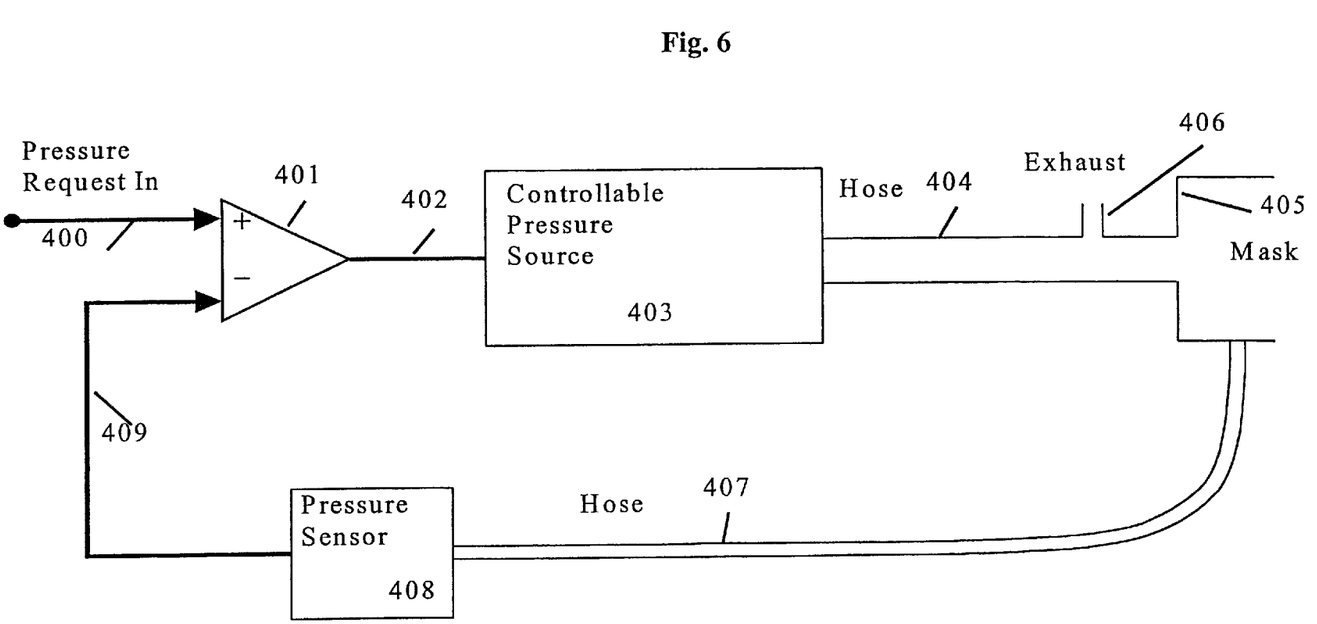

FIG. 6 shows a block diagram of a servo-controlled pressure generator and air delivery system controlled by the same pressure request output signal 304. The pressure request signal is fed to the pressure request input 400 of servo 401, whose output 402 is used to control a controllable pressure source 403 (such as a blower with variable speed motor or control valve, or compressed gas and control valve). Air (which may be enriched with oxygen) from the controllable pressure source is fed via hose 404 to mask 405 and ultimately vented through exhaust 406. A pressure sensor (transducer) 408 measures mask pressure via hose 407, and the electrical output 409 from the pressure sensor is fed back to the servo 401.

When the patient commences inspiratory effort, the pressure in the pleural cavity falls, causing the effort signal to exceed the threshold, and the higher pressure is applied. In patients with severe obstructive lung disease, requiring relatively high pressures, the intrathoracic pressure will remain negative during the patient's inspiration, because the mask pressure is not immediately transmitted to the alveoli. When the patient ceases making inspiratory effort at the end of inspiration, the intrathoracic pressure will suddenly rise, making the effort signal go back to zero, or even negative in the case of actively exhaling patients. At this point, the effort signal drops back below the threshold, and the device selects the lower pressure, permitting expiration to occur.

The same type of effort sensor signal can be used to trigger still another prior art controlled ventilator, one which exhibits what is known as spontaneous plus timed backup bilevel ventilation. With such a ventilator, the mask pressure is switched to the higher pressure if the effort signal goes above a threshold indicating start of active inspiration, and then switched back to the lower pressure when the effort signal falls below the threshold indicating end of active inspiration, as described above, but in the event that the start of active inspiration is not detected within a specified time from the start of the previous active inspiration (or alternatively, within a shorter specified time from the end of the active inspiration), a machine generated "timed" breath is delivered by switching to the higher pressure for a specified duration.

In general, the output of trigger 302 can be used to replace the trigger of any known class of ventilator, switching the ventilator from the expiratory to the inspiratory sub-cycle when the effort signal goes above a threshold, or from the expiratory to the inspiratory sub-cycle when the effort signal goes below a threshold, or both. Such ventilators include but are not limited to volume cycled ventilators, pressure support ventilators, volume servo-ventilators, and proportional assist ventilators.

3. Degree of Support Proportional to the Effort Signal, as Measured Directly Using the Effort Sensor: Effort Reducing Ventilatory Support Thus far, what has been described is the triggering of a conventional control means between an inspiratory and an expiratory state. A further aspect of my invention relates to adjusting the degree of support to be proportional to the effort signal.

The output E(t) on conductor 301 from the effort sensor 300 in FIG. 5 may be delivered to an amplifier which generates a pressure request signal P(t), such that $$P(t)=P_0+KE(t). \qquad \text{(Equation 1)}$$

This is the desired pressure, and it is equal to a bias level $P_0$ plus a pressure that is proportional to the patient's effort. The pressure request signal P(t) is then applied to the pressure request input 400 in FIG. 6. (An actual circuit for implementing this embodiment of the invention is identical to that of FIG. 5, with the difference that trigger circuit 303 is replaced by a circuit for generating the function of Equation 1.)

It is instructive to compare this embodiment of the invention (effort reducing ventilatory support) with conventional proportional assist ventilation. Proportional assist ventilation provides an instantaneous pressure which is a function of airflow f(t), as follows:

$$P(t)=P_0+Rf(t)+E\int f(t)dt, \; f(t)>0 \qquad \text{(Equation 2)}$$

$$P(t)=P_0+Rf(t), \text{ otherwise.} \qquad \text{(Equation 3)}$$

In these equations, R is the resistance of the subject's airway, and the product Rf(t) represents a desired pressure component which compensates for the way the airway impedes air flow. The term $E\int f(t)dt$ represents a desired pressure component which compensates for the elastic recoil of the patient's lungs.

A first difference between the effort reducing ventilatory support of the invention and the prior art proportional assist ventilation is that there is no need to measure respiratory airflow f(t), with its attendant problem of leaks.

A second difference is that there is no integral term with effort reducing ventilatory support, whereas with proportional assist ventilation there is such an integral term.

A third and crucial difference, which follows in part from the second difference, is that with effort reducing ventilatory support there is no triggering between two states, whereas with proportional assist ventilation (and most other known forms of ventilatory support) there is such triggering. Specifically, with proportional assist ventilation, Equations 2 and 3 define two trigger conditions. Consider for example the state of affairs at the end of an inspiration using 100% proportional assist, in which R equals the resistance of the subject's airway, and E equals the elastance of the subject's lungs and chest wall. At this moment, the term Rf(t) is zero (because airflow f(t) is zero), but the term $E\int f(t)dt$ is non-zero, and exactly balances the elastic recoil of the patient's lungs. Since expiration is passive, nothing happens. There is no airflow, and the subject cannot breathe out. It is necessary to switch to Equation 3 in order for the patient to be able to breathe out. On the other hand, in effort reducing ventilatory support (Equation 1), there is no concept of triggering between two states, an inspiratory state and an expiratory state. Again consider affairs at the end of inspiration. As soon as the subject starts to reduce inspiratory effort, the delivered pressure will start to reduce, exactly in parallel with the muscular effort. By the time the inspiratory effort is zero, the mask pressure will have returned to the minimum level $P_0$, and the degree of support will have returned to zero, as desired, with no need for a trigger. With effort reducing ventilatory support the desired pressure-controlling function does not change abruptly; rather, it changes continuously in proportion to the patient's effort (i.e., there are no trigger-controlled discontinuities).

A fourth difference from proportional assist ventilation is that in proportional assist ventilation it is necessary to either know or empirically determine values for R and E in Equation 2, the subject's airway resistance, and lung plus chest wall elastance, respectively. In particular, the use of values of R or E larger than 100% of the corresponding physiological values causes unstable run-away of the control algorithm. On the other hand, with effort reducing ventilatory support, it is not necessary to know or determine any parameters and, as will become apparent, even arbitrarily high values of the parameter K in Equation 1 can in principle be used without causing instability or runaway.

It is instructive to compare the current invention with PPAP (Proportional Positive Airway Pressure), as taught in Estes U.S. Pat. No. 5,794,615, in which the controlling equation is $$P(t)=P_0+Kf(t). \qquad \text{(Equation 4)}$$

Here, the desired variable pressure component is a function of airflow only. Although there is no trigger in Equation 4, pressure is still proportional to flow, and not to effort. The difference between PPAP and effort reducing ventilatory support is particularly apparent in the presence of high elastic work of breathing because of the very absence of a term in Equation 4 proportional to the integral of flow, which means that with PPAP, only resistive, as opposed to elastic, work is unloaded, whereas with the present invention both resistive and elastic work are unloaded. In addition, PPAP still has the problem of working incorrectly in the presence of severe or changing leak, whereas effort reducing ventilatory support is uninfluenced by leak. As with PAV (Equations 2 and 3), with PPAP (Equation 4) K must be specified to suit the patient; and large values of K lead to instability, which is not the case with the present invention.

In all forms of ventilatory support that include a trigger, factors unrelated to respiratory effort, for example, sensor noise or oscillations in intrapleural pressure due to heartbeat can cause false or premature switching between the ventilator inspiratory state (typically, a high pressure or inspiratory flow) and the ventilator expiratory state (typically, a low pressure or expiratory flow). With effort reducing ventilatory support there is no such problem. Instead, such cardiogenic pressure oscillations merely cause minor transient changes in mask pressure, which approximately cancel out the intrathoracic pressure changes caused by the heartbeat. An interesting secondary effect is that this will somewhat unload the work of the heart, and this will be of advantage to patients with cardiac failure.

4. Degree of Support Adjusted to Servo-Control Effort to be Near Zero: Effort Canceling Ventilatory Support If the gain K in effort reducing ventilatory support is sufficiently high, the control algorithm becomes a simple proportional servo-controller, in which the patient's respiratory effort is the controlled variable, and is servo controlled to be near zero (effort canceling—not just reducing—ventilatory support) by increasing the mask pressure if the effort is positive, and decreasing the mask pressure if the effort is negative.

In practice, a simple proportional controller of modest gain (for example, 10 cmH$_2$O generated pressure per 1 cmH$_2$O change in intrapleural pressure) is adequate, but a PID controller, fuzzy controller, adaptive controller, fuzzy adaptive controller, or any other known controller could also be used, in order to produce somewhat better control. In each case, the controller is simply fed with the effort signal E(t) as the controlled, or input, variable, the output from the controller is added to Po to achieve the desired instantaneous output pressure P(t), and a suitable pressure request signal is sent to the blower to generate an instantaneous mask pressure of P(t).

As previously stated, an advantage of this method is that the effort signal E(t) does not have to be linear or even calibrated, and can saturate at high effort, without interfering with useful operation. The only requirements for the device to perform usefully are that the effort signal should be approximately zero for zero effort, greater than zero for all positive efforts, and less than zero for all negative efforts.

If the effort sensor output is substantially non-zero at zero effort, the mask pressure will depart from the desired resting pressure P$_0$. The circuit of FIG. 3 solves this problem by passing the effort signal through a trough detector with a time constant long compared with a single breath but short compared with any drift in the zero value for the effort sensor, and correcting the effort sensor for zero drift by subtracting the trough signal.

The other advantages of effort reducing ventilatory support are also maintained, including no need to customize parameters for a particular patient, immunity to false triggering from cardiogenic pressure oscillations, and some degree of unloading of the work of the beating heart.

5. Other Effort Sensors and Other Sources of Ventilatory Support

In the embodiments described above, the effort sensor is an optical sensor detecting movement of the skin of the suprasternal notch. However, any other form of effort sensor could also be used, for example, invasively measured pleural or transdiaphragmatic pressure, electromyogram signals from diaphragm, intercostal, or accessory respiratory muscles, or electroneurogram signals to these muscles.

Similarly, the pressure request signal could be used to control any other kind of ventilatory support device, such as a pneumobelt, rocking bed, cuirasse, iron lung, venturi, or transtracheal ventilator.

In general, and in particular in all of the above embodiments of the invention, the pressure at end expiration, P0, can be set sufficiently high to treat coexisting obstructive sleep apnea. Such a pressure can be determined in advance using any conventional manual or automatic CPAP titration technique. Alternatively, a suitable pressure can be determined empirically during actual therapy with the current invention. During effort-canceling ventilatory support, as described in the present application, any additional pressure drop across a partially narrowed upper airway will be automatically compensated for by an equal increase in mask pressure, so it is only necessary to set P0 high enough to prevent passive collapse. The value P0 can be automatically adjusted to treat coexisting obstructive sleep apnea by calculating a measure of the conductance of the airway, for example, by using a forced oscillation method, and increasing P0 if conductance is below a threshold. During ventilatory support with the present invention, obstructive sleep apnea can be distinguished from central sleep apnea with closed vocal cords by inspecting the effort signal. If, during a period of zero respiratory airflow (apnea) the effort signal shows ongoing inspiratory efforts, then the apnea is obstructive and the end expiratory pressure should be increased. Conversely, if the effort signal reveals the absence of effort, then the apnea is central, and in general pressure should not be increased. The determination of the presence or absence of respiratory effort during an apnea, and the subsequent increase or non-increase in end expiratory pressure can be performed automatically. Finally, the value PO can be automatically increased in the event that the ratio of the effort signal to respiratory airflow is larger than a threshold, indicating an obstructive hypopnea.

Although the invention has been described with reference to particular embodiments, it is to be understood that these embodiment are merely illustrative of the application of the principles of the invention. Numerous modifications may be made therein and other arrangements may be devised without departing from the spirit and scope of the invention.

What is claimed is:

1. A method for controlling a mechanical ventilator comprising the steps of:

providing a subject with breathable gas at controllable pressure;

providing a patient mountable source of light targeting a suprasternal notch of the subject;

deriving a measure of respiratory effort from the movement of the skin of the suprasternal notch only from a reflection of light from said notch; and adjusting said controllable pressure in relation to a reference pressure in accordance with said measure of respiratory effort.

2. A method for controlling a mechanical ventilator in accordance with claim 1 wherein the controllable pressure is set to a higher pressure if the respiratory effort is inspiratory, and set to a lower pressure otherwise.

3. A method for controlling a mechanical ventilator in accordance with claim 1 wherein the controllable pressure is set to a higher pressure if the respiratory effort is inspiratory or if there has not been a transition from low to high pressure for a predetermined period of time since a previous pressure transition, and set to a lower pressure otherwise.

4. A method for controlling a mechanical ventilator in accordance with claim 1 wherein the controllable pressure is set to be an increasing function of the respiratory effort, inspiratory effort being taken as positive and expiratory effort being taken as negative.

5. A method for controlling a mechanical ventilator in accordance with claim 1 wherein the controllable pressure is set by a servo-controller, operable to servo-control the respiratory effort to be zero.

6. A method for controlling a mechanical ventilator in accordance with claim 5 wherein the controllable pressure is made equal to a chosen positive pressure when the subject is making no respiratory effort.

7. A method for controlling a mechanical ventilator in accordance with claim 1 wherein the controllable pressure is the sum of a first pressure plus a second pressure proportional to the respiratory effort.

8. The method for controlling a mechanical ventilator in accordance with claim 7 wherein said measure represents a varying degree of inspiratory and expiratory effort.

9. A method for controlling a mechanical ventilator in accordance with any of claims 1–6 wherein said measure of respiratory effort is derived by positioning a sensor that includes a light source and a photocell such that the photocell output is a function of the depth of the subject's suprasternal notch.

10. A method for controlling a mechanical ventilator comprising the steps of:
    providing a subject with breathable gas at controllable pressure;
    providing a patient mountable source of light targeting a suprasternal notch of the subject;
    deriving a measure of respiratory effort from movement of a subject's skin only as a function of light reflected from the suprasternal notch of the subject; and
    adjusting said controllable pressure to be the sum of a first pressure plus a second pressure proportional to the respiratory effort.

11. A method for controlling a mechanical ventilator in accordance with claim 10 wherein said measure of respiratory effort is derived by positioning a sensor that includes a light source and a photocell such that the photocell output is a function of the depth of the subject's suprasternal notch.

12. The method for controlling a mechanical ventilator in accordance with claim 10 wherein said measure represents a varying degree of inspiratory and expiratory effort.

13. A method for controlling a mechanical ventilator comprising the steps of:
    providing a subject with breathable gas at controllable pressure;
    providing a patient mountable source of light targeting a suprasternal notch of the subject;
    deriving a measure of a varying degree of inspiratory and expiratory respiratory effort from movement of the subject's skin only as a function of light reflected from the suprasternal notch of the subject; and
    adjusting said controllable pressure by servo-controlling the measure of the varying degree of inspiratory and expiratory respiratory effort to be zero.

14. A method for controlling a mechanical ventilator in accordance with claim 13 wherein said measure of respiratory effort is derived by positioning a sensor that includes a light source and a photocell such that the photocell output is a function of the depth of the subject's suprasternal notch.

15. A mechanical ventilator to provide ventilatory support comprising:
    a source of breathable gas at a controllable pressure for a subject;
    a patient mountable source of light targeting a suprasternal notch of the subject;
    a transducer to measure respiratory effort from movement of skin of a suprasternal notch only from a reflection of light from said notch; and
    a controller that responds to said transducer and adjusts said controllable pressure in relation to a reference pressure in accordance with the measure of respiratory effort.

16. A mechanical ventilator in accordance with claim 15 wherein the controller adjusts the pressure to a high level if the respiratory effort is inspiratory, and adjusts the pressure to a low level otherwise.

17. A mechanical ventilator in accordance with claim 15 wherein the controller adjusts the pressure higher if the respiratory effort is inspiratory or if there has not been a transition from low to high pressure for a predetermined period of time since a previous pressure transition, and adjusts the pressure lower otherwise.

18. A mechanical ventilator in accordance with claim 15 wherein the controller adjusts the pressure to be an increasing function of the respiratory effort, inspiratory effort being taken as positive and expiratory effort being taken as negative.

19. A mechanical ventilator in accordance with claim 15 wherein the controller adjusts the pressure by operating a servo-controller that servo-controls the respiratory effort to be zero.

20. A mechanical ventilator in accordance with claim 19 wherein the controller adjusts the pressure to equal a chosen positive pressure when the subject is making no respiratory effort.

21. A mechanical ventilator in accordance with claim 15 wherein the controller adjusts the pressure to equal a sum of a first pressure plus a second pressure proportional to the respiratory effort.

22. The mechanical ventilator of claim 21 wherein said measure represents a varying degree of inspiratory and expiratory effort.

23. A mechanical ventilator in accordance with any of claims 15–21 wherein the measure of respiratory effort is derived by positioning a sensor that includes a light source and a photocell such that the photocell output is a function of a depth of the subject's suprasternal notch.

24. A mechanical ventilator comprising:
    a source of breathable gas at a controllable pressure;
    a source of light mountable to the patient's body to target a suprasternal notch of the subject;
    a transducer for measuring a varying degree of inspiratory and expiratory respiratory effort from movement of a subject's skin only as a function of light reflected from the suprasternal notch of the subject; and
    a controller that responds to said transducer and adjusts said controllable pressure to be a sum of a first pressure plus a second pressure proportional to the varying degree of inspiratory and expiratory respiratory effort from said transducer.

25. A mechanical ventilator in accordance with claim 24 wherein said measure of respiratory effort is derived by positioning a sensor that includes a light source and a photocell such that the photocell output is a function of a depth of the subject's suprasternal notch.

26. A mechanical ventilator comprising:

a source of breathable gas at a controllable pressure;

a source of light mountable to the patient's body to target a suprasternal notch of the subject;

a transducer for measuring a varying degree of inspiratory and expiratory respiratory effort from movement of a subject's skin only as a function of light reflected from the suprasternal notch of the subject; and a controller that responds to said transducer and adjusts said controllable pressure by servo-controlling the varying degree of inspiratory and expiratory respiratory effort to be zero.

27. A mechanical ventilator in accordance with claim 26 wherein said measure of respiratory effort is derived by positioning a sensor that includes a light source and a photocell such that the photocell output is a function of a depth of the subject's suprasternal notch.

* * * * *